US010628552B2

(12) United States Patent
Shi et al.

(10) Patent No.: US 10,628,552 B2
(45) Date of Patent: Apr. 21, 2020

(54) SYSTEMS AND METHODS FOR UNFAULTING POINT CLOUDS

(71) Applicant: Halliburton Energy Services, Inc., Houston, TX (US)

(72) Inventors: Genbao Shi, Sugar Land, TX (US); Jeffrey Marc Yarus, Houston, TX (US); Zitao Xu, Katy, TX (US); Maurice Gehin, Missouri City, TX (US)

(73) Assignee: LANDMARK GRAPHIC CORPORATION, Houston, TX (US)

( * ) Notice: Subject to any disclaimer, the term of this patent is extended or adjusted under 35 U.S.C. 154(b) by 277 days.

(21) Appl. No.: 15/543,230

(22) PCT Filed: Jun. 7, 2016

(86) PCT No.: PCT/US2016/036189
§ 371 (c)(1),
(2) Date: Jul. 12, 2017

(87) PCT Pub. No.: WO2017/213631
PCT Pub. Date: Dec. 14, 2017

(65) Prior Publication Data
US 2018/0336309 A1 Nov. 22, 2018

(51) Int. Cl.
*G01V 1/30* (2006.01)
*G06F 19/00* (2018.01)
(Continued)

(52) U.S. Cl.
CPC ............. *G06F 19/00* (2013.01); *E21B 41/00* (2013.01); *G01V 99/005* (2013.01); *G06Q 50/02* (2013.01); *G01V 2210/642* (2013.01)

(58) Field of Classification Search
CPC ... G01V 2210/642; E21B 41/00; G06F 19/00; G06Q 50/02
See application file for complete search history.

(56) References Cited

U.S. PATENT DOCUMENTS 6,014,343 A * 1/2000 Graf .................. G01V 1/28
367/38
7,480,205 B2 1/2009 Wei
(Continued)

FOREIGN PATENT DOCUMENTS

CN 103514630 A 1/2014
WO 2011163166 A2 12/2011

OTHER PUBLICATIONS

International Search Report and Written Opinion for PCT/US2016/036189 dated Jun. 7, 2016.
(Continued)

*Primary Examiner* — Mischita L Henson

(57) ABSTRACT

A method includes generating a faulted point cloud representing a faulted geological formation including a first fault block having a first surface, a second fault block having a second surface, and a fault formed therebetween and having a fault surface, generating a first fault trace from an intersection of the first surface and the fault surface and a second fault trace from an intersection of the second surface and the fault surface, generating a first fault polygon using the first and second fault traces, generating a center polyline, generating third and fourth fault traces separated from the first and second fault traces, respectively, generating a second fault polygon using the third and fourth fault traces, expanding a first area including the first and third fault traces, expanding a second area including the second and fourth fault traces, and generating an unfaulted point cloud representing an unfaulted geological formation.

20 Claims, 10 Drawing Sheets

(51) Int. Cl.
  *G06Q 50/02* (2012.01)
  *G01V 99/00* (2009.01)
  *E21B 41/00* (2006.01)

(56) References Cited

U.S. PATENT DOCUMENTS

| | | | |
|---|---|---|---|
| 8,009,170 B2 | 8/2011 | Shi | |
| 8,294,718 B2 | 10/2012 | Shi | |
| 8,494,827 B2 | 7/2013 | Mutlu | |
| 8,655,632 B2 | 2/2014 | Moguchaya | |
| 8,660,797 B2 | 2/2014 | Xu | |
| 2006/0253759 A1* | 11/2006 | Wei | G01V 1/282 714/738 |
| 2006/0280031 A1 | 12/2006 | Chopra et al. | |
| 2008/0015784 A1* | 1/2008 | Dorn | G01V 1/30 702/16 |
| 2010/0121622 A1 | 5/2010 | Shi et al. | |
| 2011/0205844 A1 | 8/2011 | Maucec et al. | |
| 2013/0138412 A1 | 5/2013 | Shi et al. | |
| 2013/0158962 A1 | 6/2013 | Yarus et al. | |
| 2013/0261978 A1* | 10/2013 | Xu | G01V 11/00 702/11 |
| 2014/0052427 A1 | 2/2014 | Yahiaoui et al. | |
| 2015/0032431 A1 | 1/2015 | Shi et al. | |
| 2015/0081259 A1 | 3/2015 | Leahy et al. | |
| 2015/0109295 A1 | 4/2015 | Xu et al. | |
| 2015/0285950 A1 | 10/2015 | Yarus et al. | |
| 2015/0293260 A1 | 10/2015 | Ghayour et al. | |
| 2016/0116636 A1 | 4/2016 | Xu et al. | |

OTHER PUBLICATIONS

French Patent Office, Application No. 1754017, Preliminary French Search Report and Written Opinion, dated Feb. 14, 2019, 8 pages, France.

* cited by examiner

SYSTEMS AND METHODS FOR UNFAULTING POINT CLOUDS

BACKGROUND

Geological faults occur when there is a fracture along which blocks of the Earth's crust (e.g., fault blocks) on either side of the fracture move relative to one another and parallel to the fracture (e.g., a fault plane). By definition, the fault block located above the fault plane is referred to as the hanging wall block and the fault block located below the fault plane is referred to as the footwall block. Different types of faults are classified based on the orientation of the fault blocks. For example, a "normal fault" occurs when the hanging wall block moves down relative to the footwall block and may occur when there is an expansion of the crust. Alternatively, a "reverse fault" occurs when the hanging wall block moves up relative to the footwall block and occurs when the crust is compressed.

Because faults in the Earth's crust cut through geological formations and offset them, the presence of faults makes property modeling of geological formations difficult.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Embodiments disclosed herein relate generally to unfaulting geological faults in a geological formation, and more particularly, to unfaulting a geological formation represented by a point cloud and performing property modeling in the resulting unfaulted point cloud.

According to embodiments disclosed, unfaulting involves "moving" a pair of fault blocks, one from each side of a fault, to align the fault blocks with each other, and thereby minimize the fault throws due to the fault. Initially, a point cloud of a volume of the geological formation surrounding the fault is generated. The unfaulting operation is performed on each point of the point cloud to obtain an unfaulted point cloud. The unfaulted point cloud represents the pair of fault blocks as a single, unfaulted block. Thereafter, property modeling is performed in the unfaulted point cloud to estimate geological and/or geophysical properties such as lithology, porosity, acoustic impedance, permeability, or water saturation, of the unfaulted block. The values from the property modeling are then assigned back to the original, faulted point cloud to estimate the location of the geological and/or geophysical properties in the original, faulted geological formation surrounding the fault.

As used herein, "fault throw" or variations thereof refer collectively to a vertical fault throw and a horizontal fault heave.

As used herein, "unfaulting" or variations thereof refer to restoring a geological formation having a fracture that separates a pair of fault blocks to an unfaulted stated.

As used herein, "point cloud" or variations thereof refer to a set of data points representing a desired volume of a geological formation in a desired coordinate system.

As used herein, "fault throw" or variations thereof refer to a change in depth along the intersection of a geological fault with a surface.

FIGS. 1-6 are plan views progressively illustrating an example unfaulting process as applied to a geological structure in a geological formation represented in an example three-dimensional framework 100. For the purposes of discussion herein, the framework 100 is a structural model based on horizons (surfaces) and faults in the geological formation. Similar numbers used in any of FIGS. 1-6 refer to common elements or components that may not be described more than once.

Figure 1:
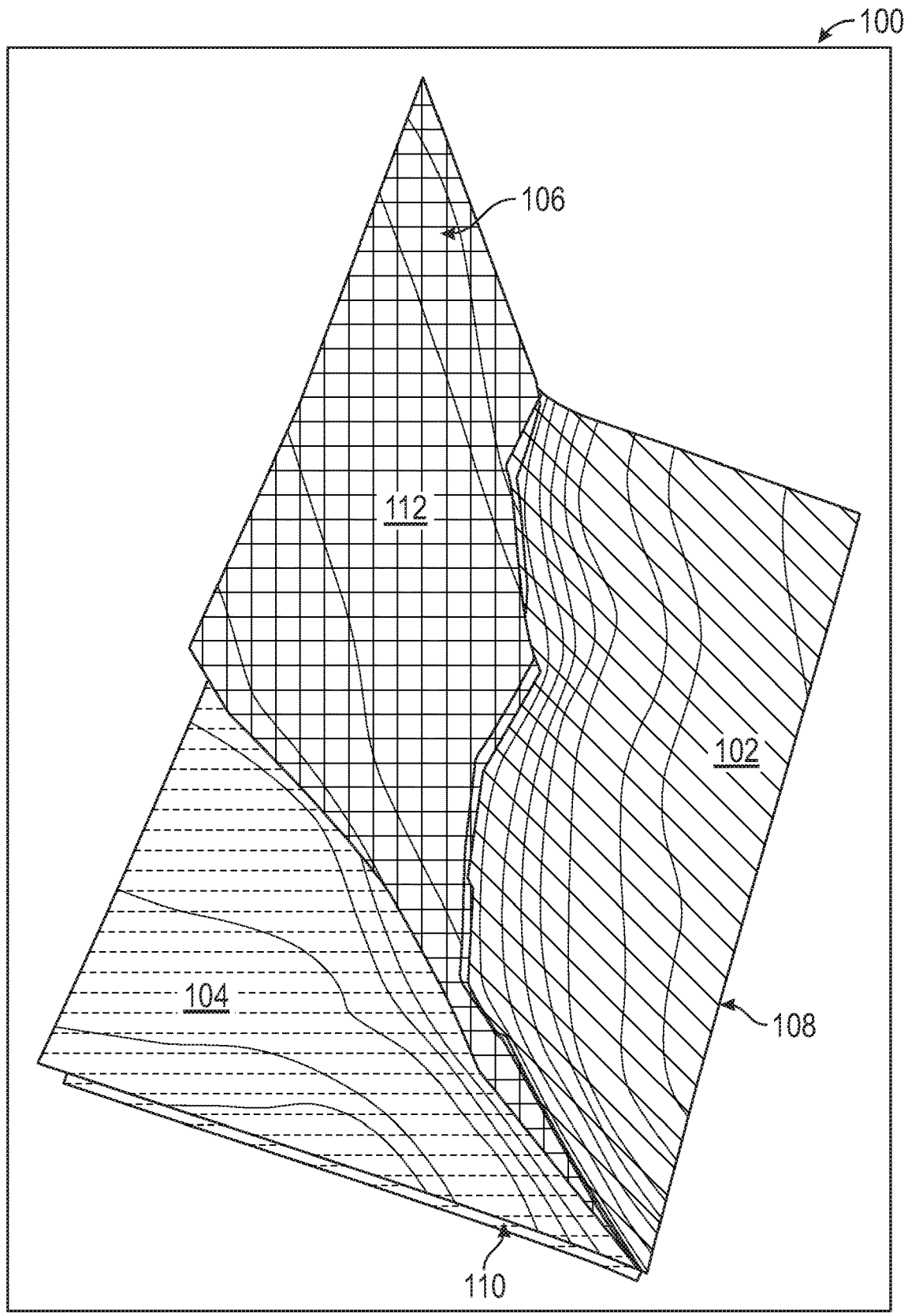
FIG. 1 is a plan view of a framework of a geological formation including surfaces of fault blocks separated by a fault.

FIG. 1 is a plan view of the framework 100 of an example geological formation (e.g., a portion of the Earth's crust) including adjacent surfaces 102 and 104, and a fault 106 between the surfaces 102 and 104. The surfaces 102 and 104 may comprise respective surfaces of two fault blocks, a hanging wall block 108 and a footwall block 110, of the Earth's crust formed due to the fault 106. As illustrated, the fault 106 defines a fracture surface 112 that intersects the surfaces 102 and 104. For the purposes of discussion herein the hanging wall block 108 refers to a fault block lying above (or on) the fracture surface 112 and the footwall block 110 refers to a fault block lying below (or underneath) the fault surface 112. Further, it is assumed that the fault 106 is a "normal fault," which is a fault where the hanging wall block 108 moves down relative to the footwall block 110.

Figure 2:
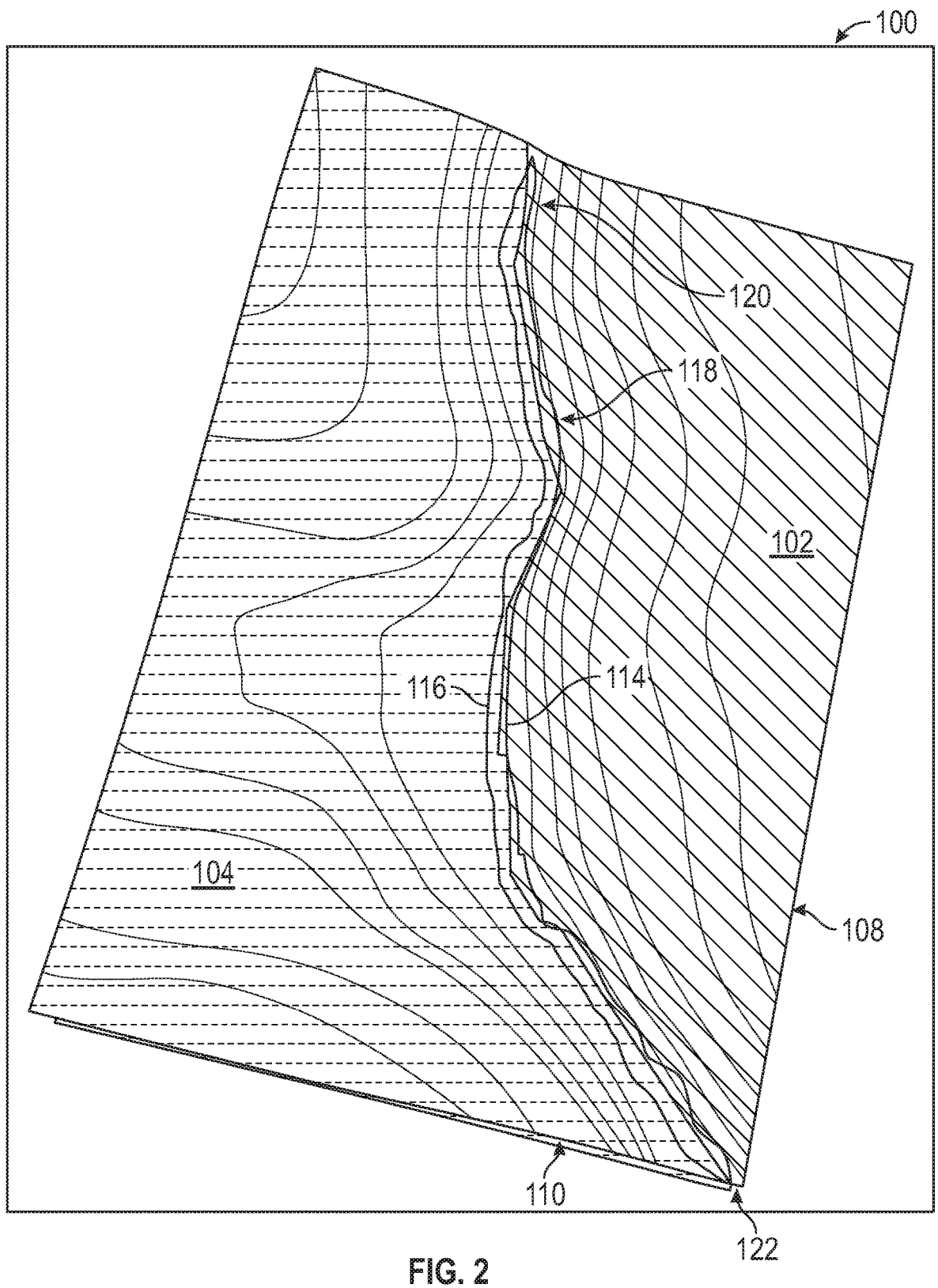
FIG. 2 is a plan view of the framework in FIG. 1 illustrating fault traces at the intersection of the fault surface and the surfaces of the fault blocks.

FIG. 2 is a plan view of the framework 100 in FIG. 1 illustrating a first fault trace 114 and a second fault trace 116 at the intersection of the fracture surface 112 (not expressly illustrated) and the surfaces 102 and 104. For the sake of simplicity of illustration, the fault 106 is omitted from FIG. 2. The first and second fault traces 114 and 116 are each represented as polylines and together define a fault polygon 118. The fault polygon 118 extends between the end-points 120 and 122 where the first and second fault traces 114 and 116 intersect.

Figure 3:
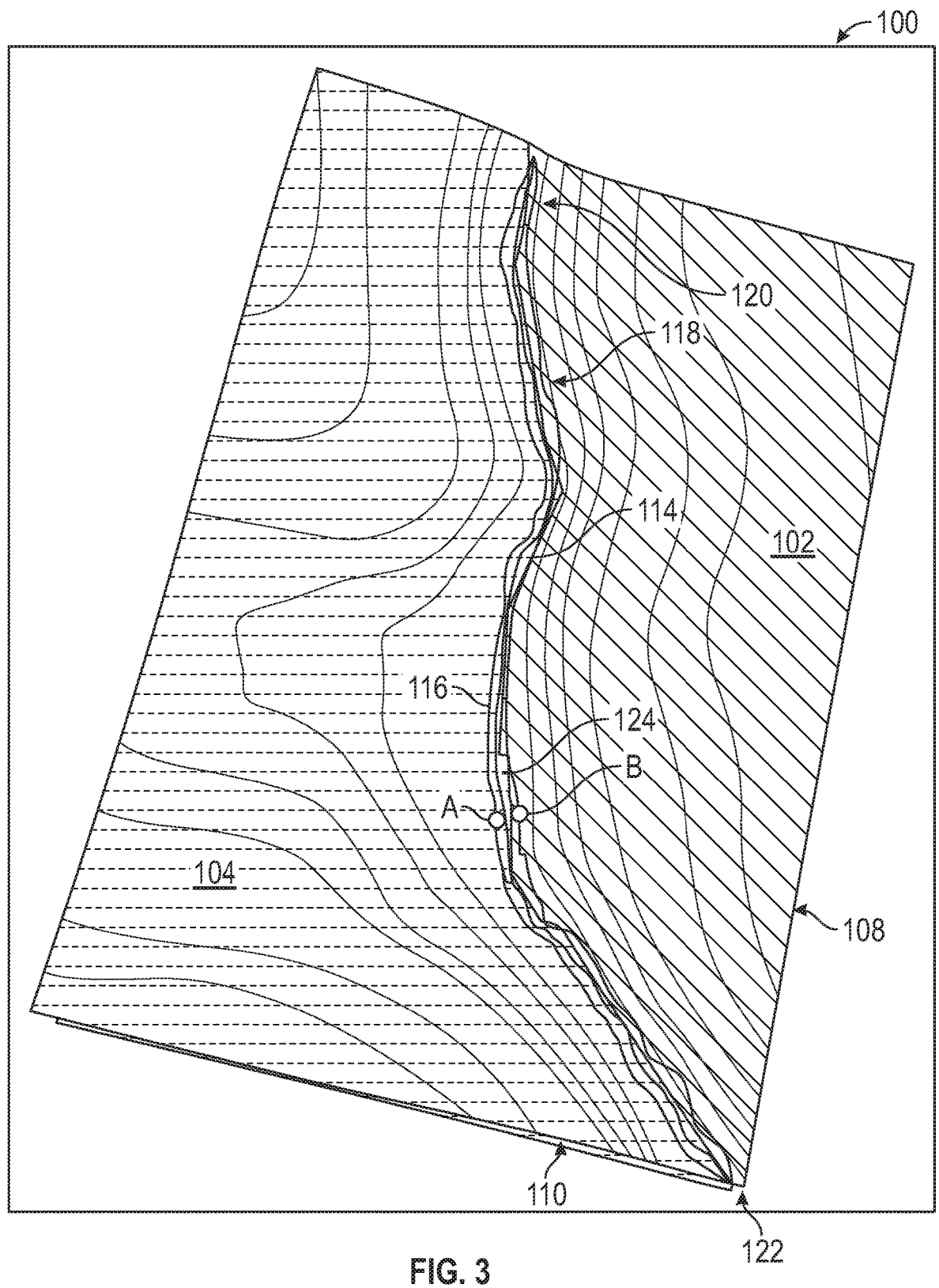
FIG. 3 illustrates a center polyline of a fault polygon formed by the fault traces in FIG. 2.

Referring to FIG. 3, the fault polygon 118 defines or otherwise provides a center polyline 124 which is a piecewise linear polyline centered in the fault polygon 118 and connecting the end-points 120 and 122. In order to determine the center polyline 124, in some embodiments, a point A is selected on the second fault trace 116 and a point B is selected on the first fault trace 114. Herein, it is assumed that the points A and B were at the same location (coincident) on the surface of the geological formation (e.g., the Earth's surface) prior to the formation of the fault 106, but are now separated due to the fault 106. A variety of known methods can be used to determine points A and B. For example, a direction of the steepest slope of the fault plane containing the fault 106 is computed and then the point B is determined by intersecting the fault trace 114 of the fault polygon 118 by a vertical plane containing both the point A and a vector representing the steepest slope.

A fault throw from point A to point B, represented by a vector $\overrightarrow{AB}$, is then determined. Using the vector $\overrightarrow{AB}$, a vector $0.5*\overrightarrow{AB}$ is calculated as the fault throw from the point A on second fault trace 116 to a first center point (not shown) on the fracture surface 112 (FIG. 1). Similarly, a vector $0.5*\overrightarrow{BA}$ is calculated as the fault throw from the point B on first fault trace 114 to a second center point (not shown) on the fault surface 112. The first and second center points thus lie on the center polyline 124. The process is repeated to obtain multiple center points along the fault polygon 118, and the line segments connecting the multiple center points form the center polyline 124. It will be understood that the above-disclosed method of obtaining the center polyline 124 is merely an example and various other methods may be used to obtain the center polyline 124, without departing from the scope of the disclosure.

The area affected by the fault 106 is then determined by creating a new fault polygon including new fault traces that are separated from the first and second fault traces 114, 116 by a known distance. In some embodiments, this known distance may be obtained from a product of the largest magnitude of all fault throws of the fault 106 and a pre-determined multiplier. The pre-determined multiplier is selected based on pre-determined criteria including, but not limited to, a size of the fault, a size of the fault throw, empirical data, and the like. For instance, if the largest magnitude of all fault throws is 10 meters and a chosen multiplier (e.g., based on pre-determined criteria) is 20, then the maximum horizontal (e.g., substantially parallel to the surfaces 102, 104) distance (or separation) between the traces forming the new fault and the first and second fault traces 114, 116 is 200 meters. Thus, a new, expanded fault polygon is obtained and includes two fault traces separated horizontally by 200 meters from first and second fault traces 114 and 116, respectively. In other instances, the pre-determined multiplier is obtained from the anisotropy ratio of the maximum horizontal continuous range to the maximum vertical continuous range of a petrophysical property, which is modeled as described in detail below. If the ratio is 100:1, then the maximum horizontal distance between the traces forming the new fault and the first and second fault traces 114, 116 is 100×(magnitude of fault throw).

Figure 4:
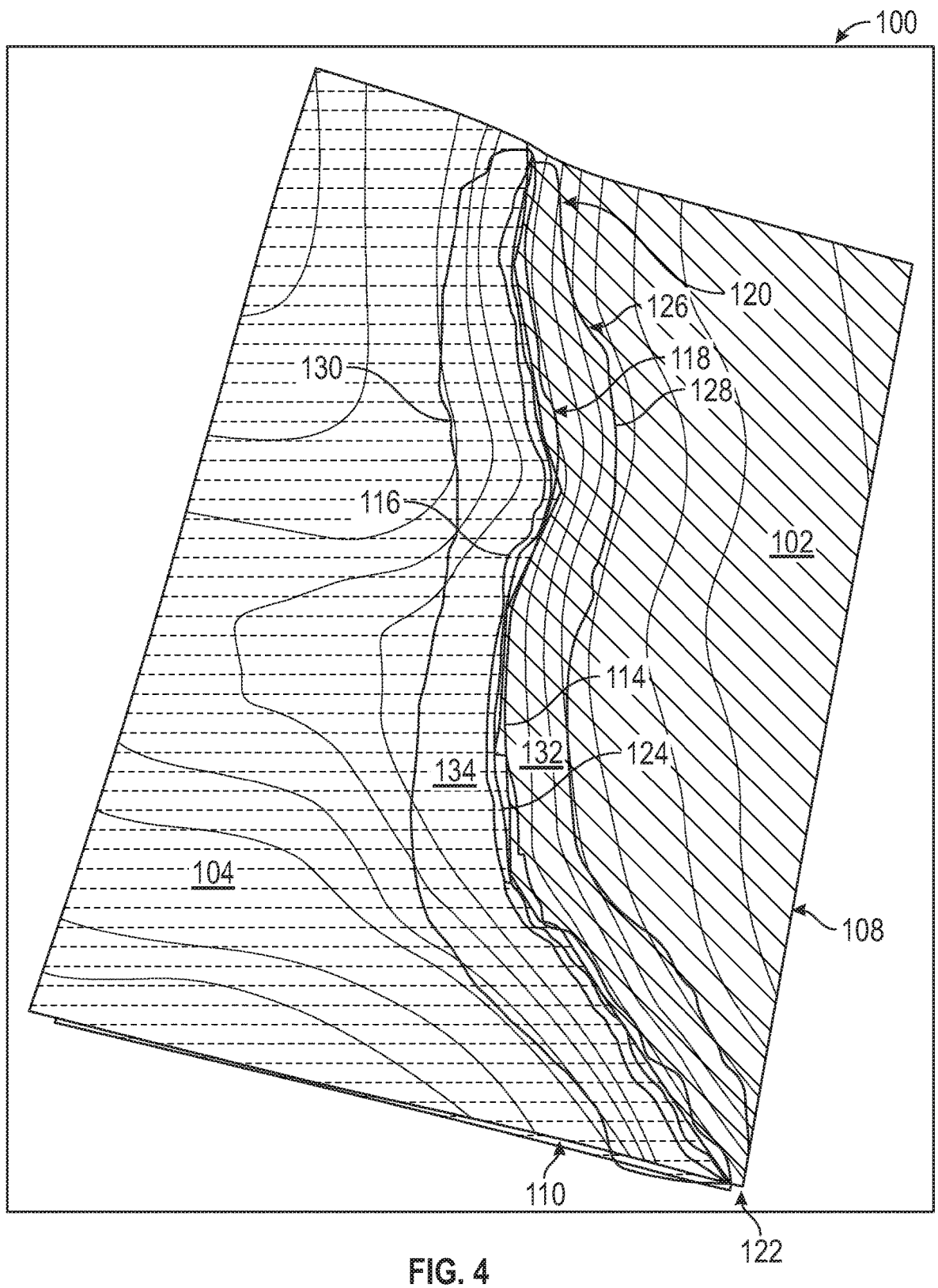
FIG. 4 illustrates an expanded fault polygon defined by fault traces, each horizontally separated from the respective fault traces in FIG. 2.

FIG. 4 illustrates an expanded fault polygon 126 formed by third and fourth fault traces 128 and 130, each horizontally separated from the respective first and second fault traces 114 and 116. The geological area included in the fault polygon 126 may be considered as the area affected by the fault 106. It will thus be understood that larger faults affect a larger area, while smaller faults affect a relatively smaller area. The affected area may be assumed to include a first area 132 bounded by the first fault trace 114 and third fault trace 128, and a second area 134 bounded by the second fault trace 116 and fourth fault traces 130.

The unfaulting process then includes expanding the first area 132 and the second area 134 to minimize or eliminate the fault throws between the first fault trace 114 and the center polyline 124, and between the second fault trace 116 and the center polyline 124. Expanding the first area 132 and the second area 134 includes a mapping process that is individually applied to the first area 132 and the second area 134 to map each point in the first area 132 and the second area 134 to a new point such that the fault throws at each of the points are removed. As a result, the fault polygon 118 and the center polyline 124 converge, and the fault 106 (FIG. 1) is removed. However, as described below, when expanding the first area 132 and the second area 134, the points on the third and fourth fault traces 128 and 130 are not mapped to new points. A variety of algorithms, such as Inverse Distance Weighting (IDW), spline interpolation, Kriging (i.e., Gaussian process regression), and the like, may be used to expand the first area 132 and the second area 134.

As a non-limiting example, the expansion of the first area 132 and the second area 134 is described herein with reference to the Kriging algorithm. It will, however, be understood that the first area 132 and the second area 134 may alternatively be expanded using the Inverse Distance Weighting (IDW), the spline interpolation algorithm, or any other suitable algorithm, without departing from the scope of the disclosure.

Kriging is an example of an unbiased interpolation algorithm and is used predict unknown values from data observed at known points (or locations). The Kriging algorithm uses variograms to express spatial variation, and minimizes the error of predicted values, which are estimated by spatial distribution of predicted values. The known locations are referred to as control points. Referring to FIGS. 3 and 4, the fault throws at the first and second fault traces 114, 116 of the fault polygon 118 and at the third and fourth fault traces 128 and 130 of the expanded fault polygon 126 are considered as the control points.

Figure 5:
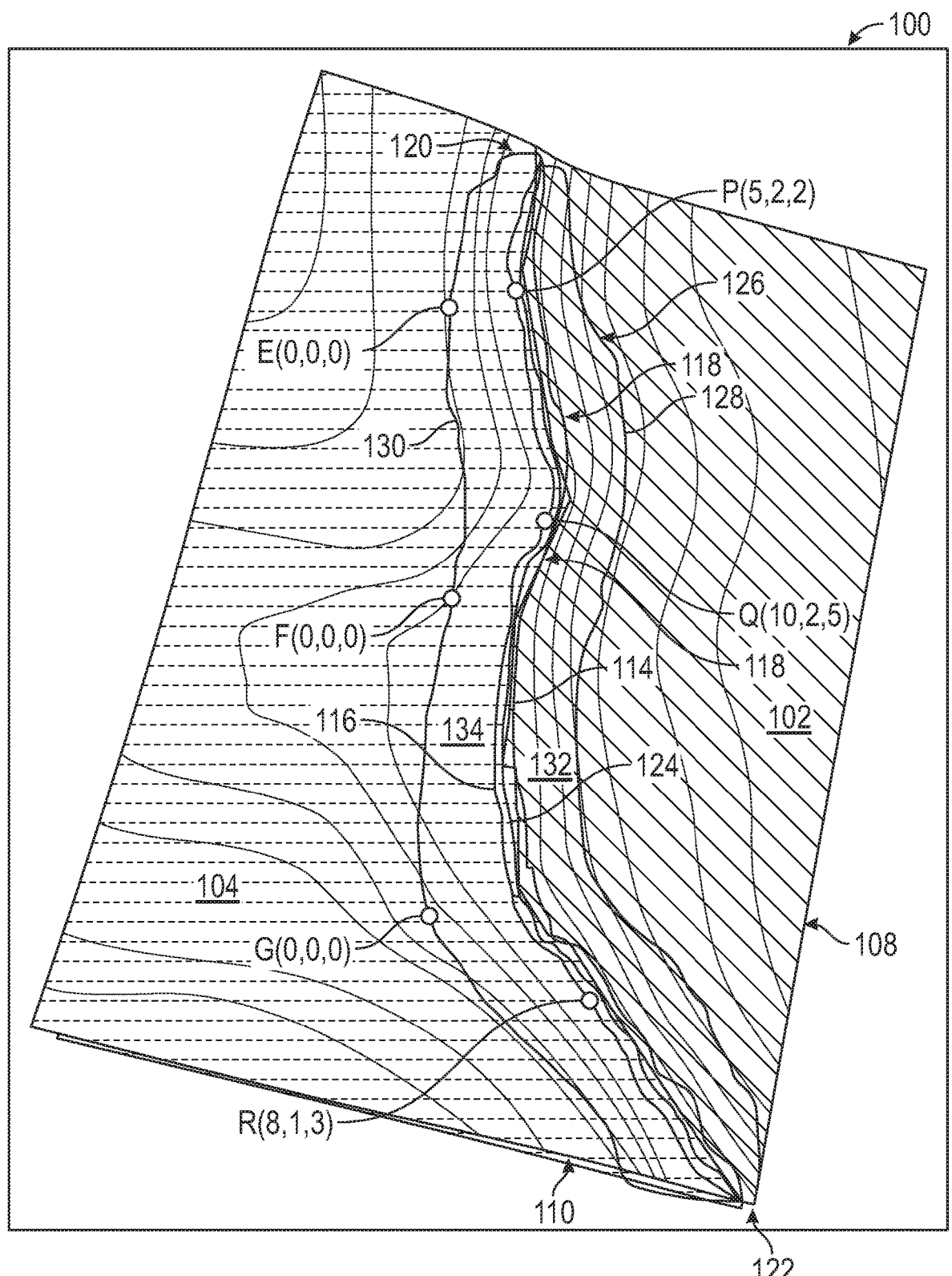
FIG. 5 illustrates the example control points of the fault traces in FIGS. 2 and 4.

FIG. 5 illustrates the fourth fault trace 130 including control points E, F, and G, each defined by the fault throw (0,0,0) and the second fault trace 116 including control points P, Q, R having fault throws (5,2,2), (10,2,5) and (8,1,3), respectively. The fault throw coordinates for the points P, Q, and R are assigned with reference to points E, F and G, respectively. The fault throw coordinates for the points P, Q, and R are mathematical representations of the vector $\overrightarrow{AB}$ between the two points E and P, F and Q, and G and R, respectively.

The Kriging algorithm may be implemented based on these six control points E, F, G, P, Q, and R. For the sake of explanation, the unfaulting process is described herein with reference to the second area 134. However, it will be appreciated that the unfaulting process may similarly be applied to the first area 132. Further, it will be understood that the number of control points chosen is merely an example, and the number of control points may be increased (or decreased) as per the desired application, without departing from the scope of the disclosure.

At each point (or location) D(x,y,z) in the second area 134, a difference vector (dx,dy,dz) is computed using the Kriging algorithm by computing the weights $w_i$ in the equations given by $$dx = \sum_{i=1}^{n} w_i * dx_i$$

-continued $$dy = \sum_{i=1}^{n} w_i * dy_i$$

$$dz = \sum_{i=1}^{n} w_i * dz_i$$

where $(dx_i, dy_i, dz_i)$ represent the corresponding fault throws (5,2,2), (10,2,5) and (8,1,3) of control points P, Q, and R, respectively, on the second fault trace 116 and the fault throws (0,0,0) of each control point E, F, and G on the fourth fault trace 130.

The difference vector (dx,dy,dz) is then added to each point D(x,y,z) in the second area 134 to map each point D(x,y,z) to a new point D' that is closer to the center polyline 124 compared to the point D(x,y,z). In other words, the point D may be said to have been moved to point D'(x+dx,y+dy,z+dz). The difference vector (dx,dy,dz) computed for each control point E, F, and F is (0,0,0), and thus the control points E, F, and G are not mapped to new points. Stated otherwise, the control points E, F, and G are "anchored." The difference vector (dx,dy,dz) is computed for the control points P, Q, and R by multiplying the fault throws (5,2,2), (10,2,5) and (8,1,3) at the respective control points P, Q, and R by 0.5. Adding the difference vector (dx,dy,dz) to the control points P, Q, and R results in the second fault trace 116 coinciding with the center polyline 124.

The above unfaulting process can similarly be applied to the first area 132. Briefly, in the unfaulting process applied to the first area 132, the control points on the third fault trace 128 are "anchored." The difference vector computed using the Kriging algorithm for each point in the first area 132 is subtracted from each point to map each point to corresponding new points that are closer to the first fault trace 114. Adding the difference vector to the control points on the first fault trace 114 results in the first fault trace 114 coinciding with the center polyline 124. The above mapping process thus removes the fault polygon 118 and, as a result, the fault 106 is removed.

Figure 6:
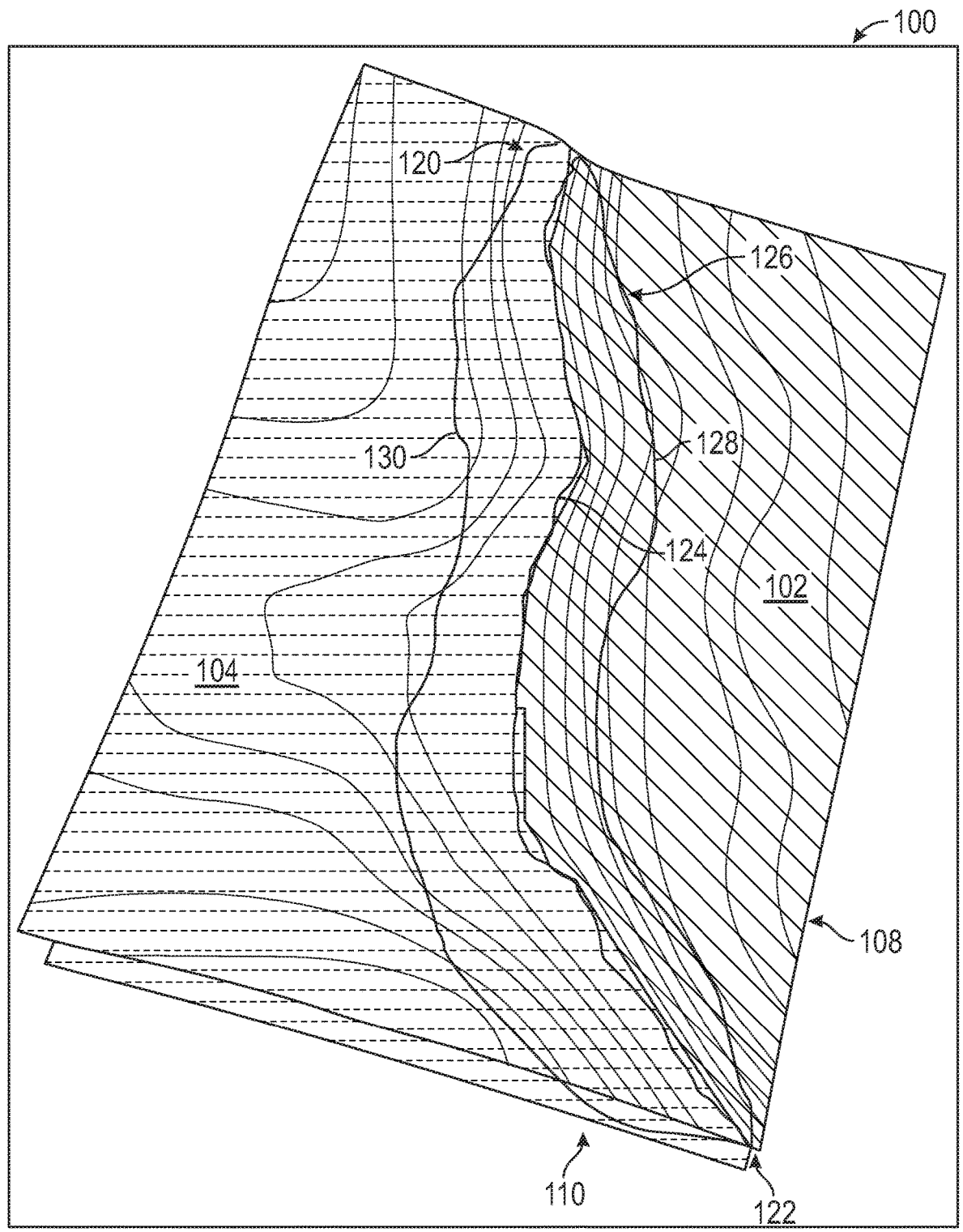
FIG. 6 illustrates the framework with the fault polygon in FIG. 3 removed.

FIG. 6 illustrates the framework 100 with the fault polygon 118 removed.

According to embodiments disclosed, the above-mentioned unfaulting process in FIGS. 1-6 can be applied to a point cloud representing the volume of a geological formation including one or more faults. Typically, the point cloud is a large collection of points acquired by 3D laser scanners or other technologies to create 3D representations of existing structures.

Figure 7:
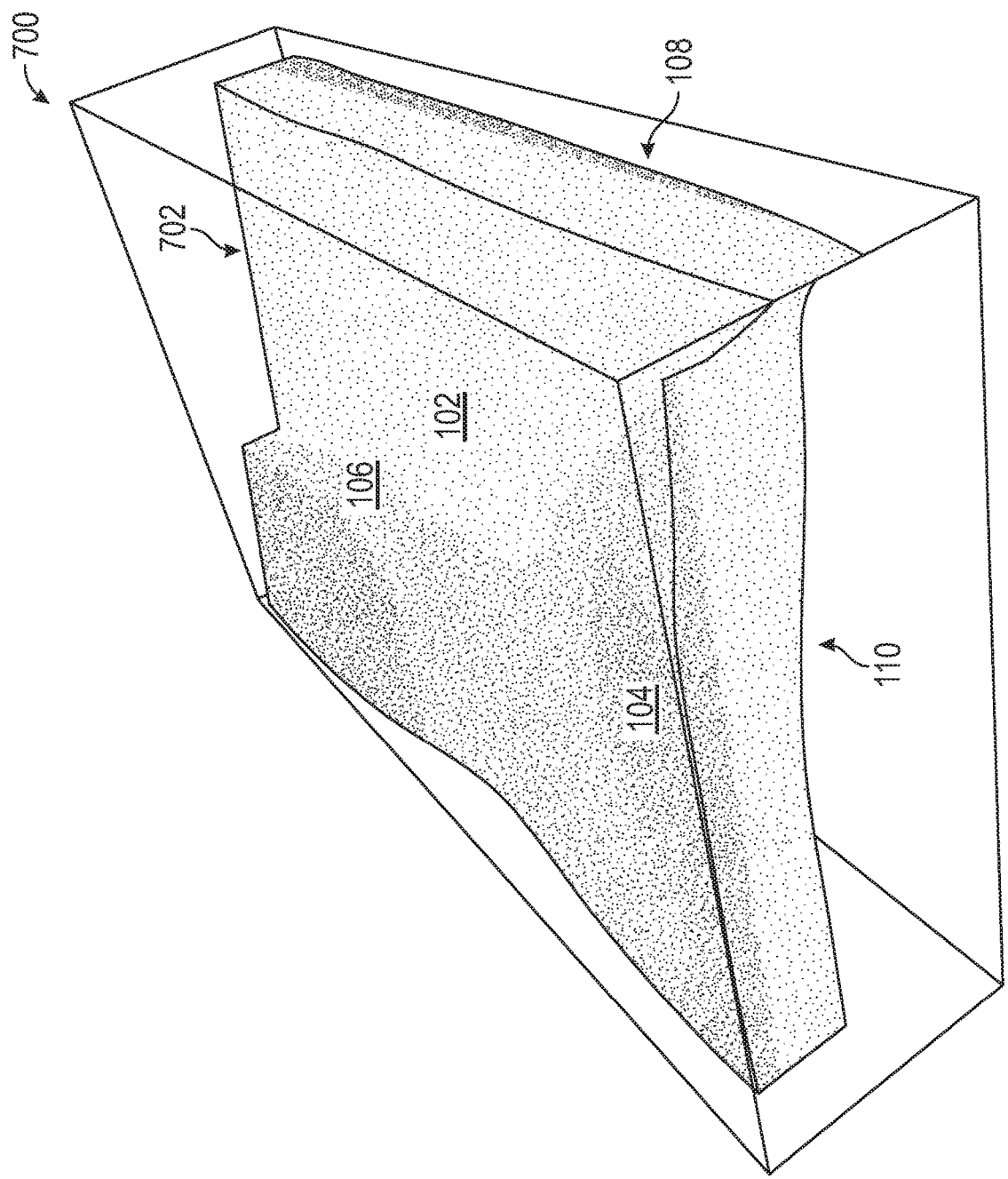
FIG. 7 illustrates a faulted point cloud of the geological formation in FIG. 1.

FIG. 7 illustrates a 3D point cloud 702 of a geological formation inside a framework 700. For the purposes of discussion herein, point cloud 702 is of the geological formation in the framework 100 of FIGS. 1-6. As illustrated, the point cloud 702 includes the surfaces 102, 104 of the hanging wall block 108 and the footwall block 110 of the Earth's crust formed due to the fault 106. The unfaulting process described above is performed on each point of the point cloud 702 to substantially align the surfaces 102 and 104 horizontally and vertically so that each surface 102, 104 transitions to the other without substantial geological/geographical variation, and thereby eliminate the fault 106. Stated otherwise, the surfaces 102 and 104 are substantially aligned such that they are merged to become a single block that may represent the geological formation prior to the fault 106.

Figure 8:
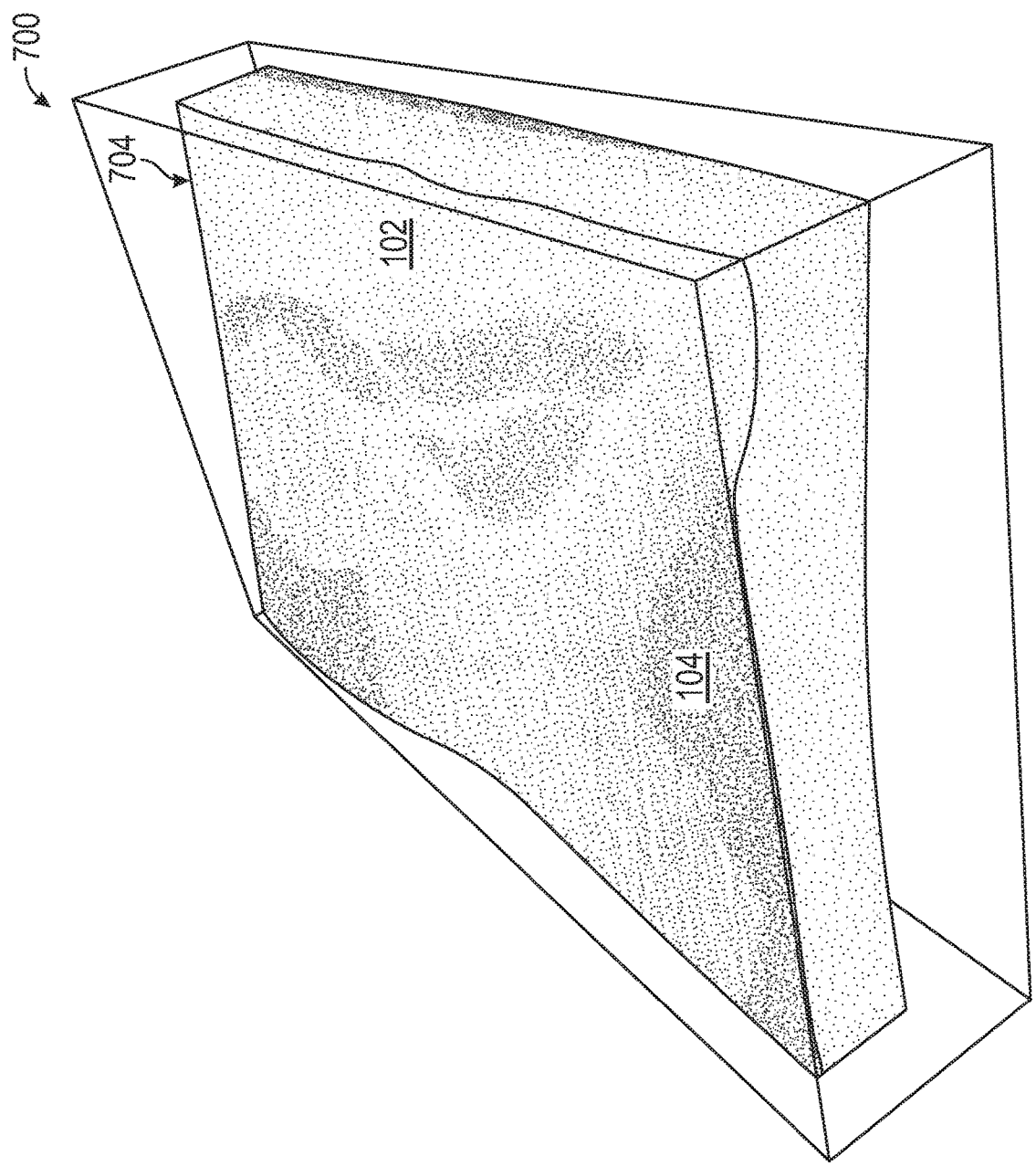
FIG. 8 illustrates an unfaulted point cloud of the geological formation in FIG. 1.

FIG. 8 illustrates an unfaulted point cloud 704 after the unfaulting process. As illustrated, the surfaces 102 and 104 are merged to become a single block that may represent the geological formation prior to formation of the fault 106. Property modeling may then be performed in the unfaulted point cloud 704 to estimate one or more geological and/or geophysical properties such as lithology, porosity, acoustic impedance, permeability, water saturation, and the like, of the geological formation. Property modeling refers to the process of assigning property values to the geological formation between multiple wells based on the various physical, chemical, electrical, or other properties of the geological formation obtained from logging operations performed in the multiple wells.

Thus, prior to performing property modeling of the unfaulted geological formation, the geological and/or geophysical properties of the faulted geological formation are obtained using desired well logging operations. The geological and/or geophysical properties of the formation from the well logging operations are incorporated in the faulted point cloud 702.

The points in the same layer of the point cloud 702 have similar properties because the layers were deposited during the same geological event. Adjacent points in the same layer across the fault 106 have similar properties because, when the layers were deposited, the fault 106 did not exist. However, the layers in the point cloud 702 may now be displaced horizontally and vertically due to the fault 106.

Unfaulting the point cloud 702 substantially aligns the layers across the fault 706 and the unfaulted point cloud 704 thus represents the geological formation prior to the generation of the fault 106. Property modeling is then performed in the unfaulted point cloud 704. The values from the property modeling are then assigned back to the faulted point cloud 702. As a result, the geological and/or geophysical properties of the faulted geological formation are obtained. In some examples, the property modeling may be performed using sequential-simulation procedures such as Sequential Gaussian simulation (SGS), Sequential indicator simulation (SIS), Bayesian indicator simulation, and the like.

Figure 9:
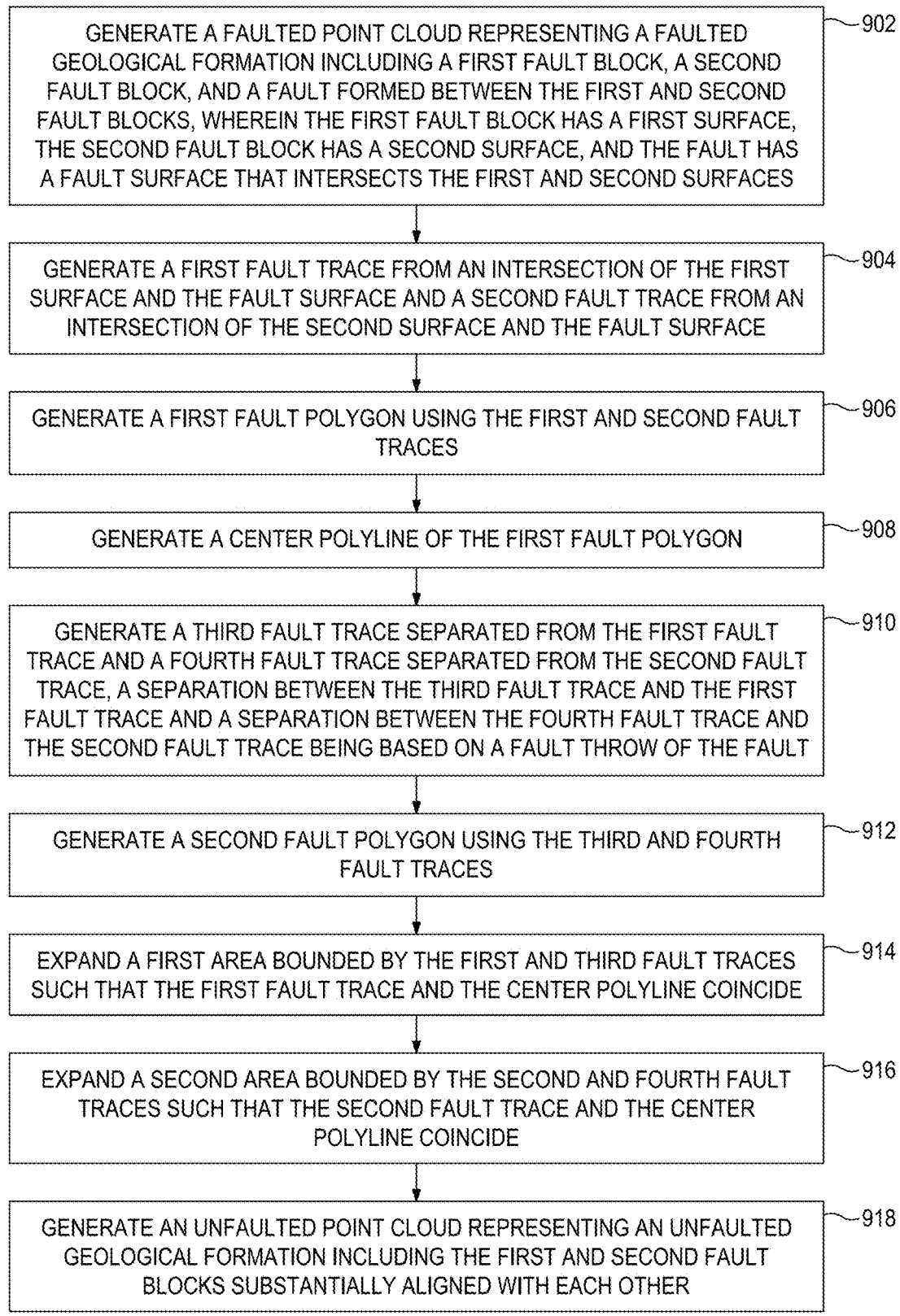
FIG. 9 is a flow diagram of an example method of unfaulting a geological formation using a point cloud.

FIG. 9 is a flow diagram of an example method 900 of unfaulting a geological formation using a point cloud. The method 900 includes generating a faulted point cloud representing a faulted geological formation including a first fault block, a second fault block, and a fault formed between the first and second fault blocks, as at 902. The first fault block has a first surface, the second fault block has a second surface, and the fault has a fault surface that intersects the first and second surfaces. The method 900 further includes generating a first fault trace from an intersection of the first surface and the fault surface and a second fault trace from an intersection of the second surface and the fault surface, as at 904, generating a first fault polygon using the first and second fault traces, as at 906, generating a center polyline of the first fault polygon, as at 908, and generating a third fault trace separated from the first fault trace and a fourth fault trace separated from the second fault trace, as at 910. A separation between the third fault trace and the first fault trace and a separation between the fourth fault trace and the second fault trace is based on a fault throw of the fault. The method 900 still further includes generating a second fault polygon using the third and fourth fault traces, as at 912, expanding a first area bounded by the first and third fault traces such that the first fault trace and the center polyline coincide, as at 914, expanding a second area bounded by the second and fourth fault traces such that the second fault trace and the center polyline coincide, as at 916, and generating an unfaulted point cloud representing an unfaulted geological formation including the first and second fault blocks substantially aligned with each other, as at 918.

Figure 10:
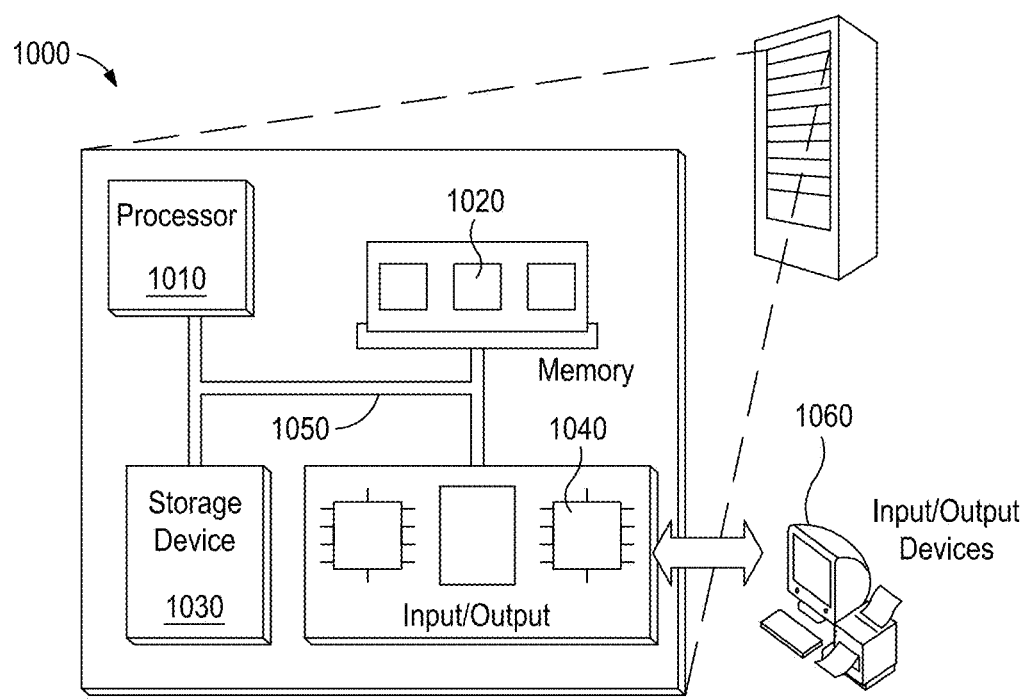
FIG. 10 shows an illustrative processing system for performing the unfaulting process using a point cloud and other tasks as described herein.

FIG. 10 shows an illustrative processing system 1000 for performing the unfaulting process described above using a point cloud and other tasks as described herein. The processing system 1000 may include a processor 1010, a memory 1020, a storage device 1030, and an input/output device 1040. Each of the components 1010, 1020, 1030, and 1040 may be interconnected, for example, using a system bus 1050. The processor 1010 may be processing instructions for execution within the processing system 1000. In some embodiments, the processor 1010 is a single-threaded processor, a multi-threaded processor, or another type of processor. The processor 1010 may be capable of processing instructions stored in the memory 1020 or on the storage device 1030. The memory 1020 and the storage device 1030 can store information within the processing system 1000.

The input/output device 1040 may provide input/output operations for the processing system 1000. In some embodiments, the input/output device 1040 can include one or more network interface devices, e.g., an Ethernet card; a serial communication device, e.g., an RS-232 port; and/or a wireless interface device, e.g., an 802.11 card, a 3G wireless modem, or a 4G wireless modem. In some embodiments, the input/output device can include driver devices configured to receive input data and send output data to other input/output devices, e.g., keyboard, printer and display devices 1060. In some embodiments, mobile computing devices, mobile communication devices, and other devices can be used.

In accordance with at least some embodiments, the disclosed methods and systems related to scanning and analyzing material may be implemented in digital electronic circuitry, or in computer software, firmware, or hardware, including the structures disclosed in this specification and their structural equivalents, or in combinations of one or more of them. Computer software may include, for example, one or more modules of instructions, encoded on computer-readable storage medium for execution by, or to control the operation of, a data processing apparatus. Examples of a computer-readable storage medium include non-transitory medium such as random access memory (RAM) devices, read only memory (ROM) devices, optical devices (e.g., CDs or DVDs), and disk drives.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing, and grid computing infrastructures.

A computer program (also known as a program, software, software application, script, or code) can be written in any form of programming language, including compiled or interpreted languages, declarative, or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be executed on one computer or on multiple computers that are located at one site or distributed across multiple sites and interconnected by a communication network.

Some of the processes and logic flows described in this specification may be performed by one or more programmable processors executing one or more computer programs to perform actions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors and processors of any kind of digital computer. Generally, a processor will receive instructions and data from a read-only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer may not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations may be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Embodiments disclosed herein include:

A. A method that includes generating a faulted point cloud representing a faulted geological formation including a first fault block, a second fault block, and a fault formed between the first and second fault blocks, wherein the first fault block has a first surface, the second fault block has a second surface, and the fault has a fault surface that intersects the first and second surfaces, generating a first fault trace from an intersection of the first surface and the fault surface and a second fault trace from an intersection of the second surface and the fault surface, generating a first fault polygon using the first and second fault traces, generating a center polyline of the first fault polygon, generating a third fault trace separated from the first fault trace and a fourth fault trace separated from the second fault trace, a separation between the third fault trace and the first fault trace and a separation between the fourth fault trace and the second fault trace being based on a fault throw of the fault, generating a second fault polygon using the third and fourth fault traces, expanding a first area bounded by the first and third fault traces such that the first fault trace and the center polyline coincide, expanding a second area bounded by the second and fourth fault traces such that the second fault trace and the center polyline coincide, and generating an unfaulted point cloud representing an unfaulted geological formation including the first and second fault blocks substantially aligned with each other.

B. A computer program product comprising a non-transitory computer readable medium having computer readable computer program code stored thereon that, when executed by a computing device, configures the computing device to generate a faulted point cloud representing a faulted geological formation including a first fault block, a second fault block, and a fault formed between the first and second fault blocks, wherein the first fault block has a first surface, the second fault block has a second surface, and the fault has a fault surface that intersects the first and second surfaces, generate a first fault trace from an intersection of the first surface and the fault surface and a second fault trace from an intersection of the second surface and the fault surface, generate a first fault polygon using the first and second fault traces, generate a center polyline of the first fault polygon, generate a third fault trace separated from the first fault trace and a fourth fault trace separated from the second fault trace, a separation between the third fault trace and the first fault trace and a separation between the fourth fault trace and the second fault trace being based on a fault throw of the fault, generate a second fault polygon using the third and fourth fault traces, expand a first area bounded by the first and third fault traces such that the first fault trace and the center polyline coincide, expand a second area bounded by the second and fourth fault traces such that the second fault trace and the center polyline coincide, and generate an unfaulted point cloud representing an unfaulted geological formation including the first and second fault blocks substantially aligned with each other.

Each of embodiments A and B may have one or more of the following additional elements in any combination: Element 1: wherein expanding the first area further comprises maintaining a location of the third fault trace. Element 2: wherein expanding the second area further comprises maintaining a location of the fourth fault trace. Element 3: wherein expanding the first area further comprises mapping each point of the faulted point cloud inside the first area to a new point in the faulted point cloud using an algorithm. Element 4: wherein the algorithm comprises at least one of Inverse Distance Weighting (IDW), spline interpolation, and Kriging. Element 5: wherein expanding the second area further comprises mapping each point of the faulted point cloud inside the second area to a new point in the faulted point cloud using an algorithm. Element 6: wherein the algorithm comprises at least one of Inverse Distance Weighting (IDW), spline interpolation, and Kriging. Element 7: wherein the third fault trace is horizontally separated from the first fault trace, and the method further comprises calculating a horizontal separation between the third fault trace and the first fault trace based on a product of the largest magnitude of fault throws of the fault and a pre-determined multiplier. Element 8: wherein the fourth fault trace is horizontally separated from the second fault trace, and the method further comprises calculating a horizontal separation between the fourth fault trace and the second fault trace based on a product of the largest magnitude of fault throws of the fault and a pre-determined multiplier. Element 9: further comprising modeling a property of the geological formation using the unfaulted point cloud. Element 10: further comprising assigning values obtained from the property modeling to the faulted point cloud.

Element 11: wherein executing the program code further configures the computing device to expand the first area while maintaining a location of the third fault trace. Element 12: wherein executing the program code further configures the computing device to expand the second area while maintaining a location of the fourth fault trace. Element 13: wherein executing the program code further configures the computing device to expand the first area by mapping each point of the faulted point cloud inside the first area to a new point in the faulted point cloud using a desired algorithm. Element 14: wherein executing the program code further configures the computing device to expand the second area by mapping each point of the faulted point cloud inside the second area to a new point in the faulted point cloud using a desired algorithm. Element 15: wherein the third fault trace is horizontally separated from the first fault trace and executing the program code further configures the computing device to calculate a horizontal separation between the third fault trace and the first fault trace based on a product of the largest magnitude of fault throws of the fault and a pre-determined multiplier. Element 16: wherein the fourth fault trace is horizontally separated from the second fault trace and executing the program code further configures the computing device to calculate a horizontal separation between the fourth fault trace and the second fault trace based on a product of the largest magnitude of fault throws of the fault and a pre-determined multiplier. Element 17: wherein executing the program code further configures the computing device to model a property of the geological formation using the unfaulted point cloud. Element 18: wherein executing the program code further configures the computing device to assign values obtained from the property modeling to the faulted point cloud.

By way of non-limiting embodiment, example combinations applicable to A and B include: Element 3 with Element 4; Element 5 with Element 6; Element 9 with Element 10; and Element 17 with Element 18.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A computer-implemented method of unfaulting point clouds, the method comprising:
    generating, by a computer system, a faulted point cloud with a set of data points representing a faulted geological formation including a first fault block, a second fault block, and a fault formed between the first and second fault blocks, wherein the first fault block has a first surface, the second fault block has a second surface, and the fault has a fault surface that intersects the first and second surfaces;
    generating, by the computer system, a first fault trace from an intersection of the first surface and the fault surface and a second fault trace from an intersection of the second surface and the fault surface;
    generating a first fault polygon using the first and second fault traces;
    generating a center polyline of the first fault polygon, based on selected data points of the faulted point cloud corresponding to the first and second fault traces;
    generating a third fault trace separated from the first fault trace and a fourth fault trace separated from the second fault trace, based on the center polyline of the first fault polygon, a separation between the third fault trace and the first fault trace and a separation between the fourth fault trace and the second fault trace being based on a fault throw of the fault;
    generating a second fault polygon using the third and fourth fault traces;
    expanding a first area of the second fault polygon bounded by the first and third fault traces by mapping data points of the faulted point cloud inside the first area to new data points such that the first fault trace and the center polyline coincide and the fault throw between the first fault trace and the center polyline is removed;
    expanding a second area of the second fault polygon bounded by the second and fourth fault traces by mapping data points of the faulted point cloud inside the second area to new data points such that the second fault trace and the center polyline coincide and the fault throw between the second fault trace and the center polyline is removed;
    generating an unfaulted point cloud representing an unfaulted state of the faulted geological formation including the first and second fault blocks substantially aligned with each other; and
    estimating geophysical properties of the faulted geological formation using the generated unfaulted point cloud.

2. The method of claim 1, wherein expanding the first area further comprises maintaining a location of the third fault trace.

3. The method of claim 1, wherein expanding the second area further comprises maintaining a location of the fourth fault trace.

4. The method of claim 1, wherein the data points of the faulted point cloud inside the first area are mapped to new data points using an algorithm.

5. The method of claim 4, wherein the algorithm comprises at least one of Inverse Distance Weighting (IDW), spline interpolation, and Kriging.

6. The method of claim 1, wherein the data points of the faulted point cloud inside the second area are mapped to new data points using an algorithm.

7. The method of claim 6, wherein the algorithm comprises at least one of Inverse Distance Weighting (IDW), spline interpolation, and Kriging.

8. The method of claim 1, wherein the third fault trace is horizontally separated from the first fault trace, and the method further comprises calculating a horizontal separation between the third fault trace and the first fault trace based on a product of the largest magnitude of fault throws of the fault and a pre-determined multiplier.

9. The method of claim 1, wherein the fourth fault trace is horizontally separated from the second fault trace, and the method further comprises calculating a horizontal separation between the fourth fault trace and the second fault trace based on a product of the largest magnitude of fault throws of the fault and a pre-determined multiplier.

10. The method of claim 1, further comprising modeling a property of the geological formation using the unfaulted point cloud.

11. The method of claim 10, further comprising assigning values obtained from the property modeling to the faulted point cloud.

12. A computer program product comprising a non-transitory computer readable medium having computer readable computer program code stored thereon that, when executed by a computing device, configures the computing device to:
    generate a faulted point cloud with a set of data points representing a faulted geological formation including a first fault block, a second fault block, and a fault formed between the first and second fault blocks, wherein the first fault block has a first surface, the second fault block has a second surface, and the fault has a fault surface that intersects the first and second surfaces;
    generate a first fault trace from an intersection of the first surface and the fault surface and a second fault trace from an intersection of the second surface and the fault surface;
    generate a first fault polygon using the first and second fault traces;

generate a center polyline of the first fault polygon, based on selected data points of the faulted point cloud corresponding to the first and second fault traces;

generate a third fault trace separated from the first fault trace and a fourth fault trace separated from the second fault trace, based on the center polyline of the first fault polygon, a separation between the third fault trace and the first fault trace and a separation between the fourth fault trace and the second fault trace being based on a fault throw of the fault;

generate a second fault polygon using the third and fourth fault traces;

expand a first area of the second fault polygon bounded by the first and third fault traces by mapping data points of the faulted point cloud inside the first area to new data points such that the first fault trace and the center polyline coincide and the fault throw between the first fault trace and the center polyline is removed;

expand a second area of the second fault polygon bounded by the second and fourth fault traces by mapping data points of the faulted point cloud inside the second area to new data points such that the second fault trace and the center polyline coincide and the fault throw between the second fault trace and the center polyline is removed;

generate an unfaulted point cloud representing an unfaulted state of the faulted geological formation including the first and second fault blocks substantially aligned with each other; and estimate geophysical properties of the faulted geological formation using the generated unfaulted point cloud.

13. The computer program product of claim 12, wherein executing the program code further configures the computing device to expand the first area while maintaining a location of the third fault trace.

14. The computer program product of claim 12, wherein executing the program code further configures the computing device to expand the second area while maintaining a location of the fourth fault trace.

15. The computer program product of claim 12, wherein executing the program code further configures the computing device to map the data points of the faulted point cloud inside the first area to new data points using a desired algorithm.

16. The computer program product of claim 12, wherein executing the program code further configures the computing device to map the data points of the faulted point cloud inside the second area to new data points using a desired algorithm.

17. The computer program product of claim 12, wherein the third fault trace is horizontally separated from the first fault trace and executing the program code further configures the computing device to calculate a horizontal separation between the third fault trace and the first fault trace based on a product of the largest magnitude of fault throws of the fault and a pre-determined multiplier.

18. The computer program product of claim 12, wherein the fourth fault trace is horizontally separated from the second fault trace and executing the program code further configures the computing device to calculate a horizontal separation between the fourth fault trace and the second fault trace based on a product of the largest magnitude of fault throws of the fault and a pre-determined multiplier.

19. The computer program product of claim 12, wherein executing the program code further configures the computing device to model a property of the geological formation using the unfaulted point cloud.

20. The computer program product of claim 19, wherein executing the program code further configures the computing device to assign values obtained from the property modeling to the faulted point cloud.

\* \* \* \* \*

UNITED STATES PATENT AND TRADEMARK OFFICE
CERTIFICATE OF CORRECTION

PATENT NO. : 10,628,552 B2
APPLICATION NO. : 15/543230
DATED : April 21, 2020
INVENTOR(S) : Genbao Shi et al.

It is certified that error appears in the above-identified patent and that said Letters Patent is hereby corrected as shown below:

On the Title Page

Item (73), change "GRAPHIC" to -- GRAPHICS --

Signed and Sealed this
Seventh Day of February, 2023

Katherine Kelly Vidal
*Director of the United States Patent and Trademark Office*